US008673339B2

(12) United States Patent
Stokes et al.

(10) Patent No.: US 8,673,339 B2
(45) Date of Patent: *Mar. 18, 2014

(54) DEMAND-RELEASE BIOACTIVE COMPOSITION FOR IMPLANTABLE MEDICAL DEVICES

(75) Inventors: Kenneth B. Stokes, Anoka, MN (US); Michael J. Ebert, Fridley, MN (US); Christopher M. Hobot, Tonka Bay, MN (US)

(73) Assignee: Medtronic, Inc., Minneapolis, MN (US)

( * ) Notice: Subject to any disclaimer, the term of this patent is extended or adjusted under 35 U.S.C. 154(b) by 1784 days.

This patent is subject to a terminal disclaimer.

(21) Appl. No.: 10/386,967

(22) Filed: Mar. 11, 2003

(65) Prior Publication Data

US 2004/0180073 A1 Sep. 16, 2004

(51) Int. Cl.
*A61F 2/00* (2006.01)
*A61K 9/00* (2006.01)

(52) U.S. Cl.
USPC .................. 424/426; 424/423; 424/400

(58) Field of Classification Search
None
See application file for complete search history.

(56) References Cited

U.S. PATENT DOCUMENTS

| 3,876,729 | A | * | 4/1975 | Mueller ..................... 525/276 |
| 4,346,709 | A | | 8/1982 | Schmitt |
| 4,506,680 | A | | 3/1985 | Stokes |
| 4,577,642 | A | | 3/1986 | Stokes |
| 4,606,118 | A | | 8/1986 | Cannon et al. |
| 5,047,456 | A | * | 9/1991 | Onwumere et al. ........... 524/13 |
| 5,342,693 | A | | 8/1994 | Winters et al. |
| 5,589,563 | A | | 12/1996 | Ward et al. |
| 5,652,014 | A | * | 7/1997 | Galin et al. ................. 427/2.24 |
| 5,837,008 | A | | 11/1998 | Berg et al. |
| 5,877,263 | A | * | 3/1999 | Patnaik et al. ............... 525/453 |
| 5,980,927 | A | | 11/1999 | Nelson et al. |
| 5,987,746 | A | | 11/1999 | Williams |
| 6,107,416 | A | | 8/2000 | Patnaik et al. |
| 6,110,155 | A | | 8/2000 | Baudino |
| 6,968,234 | B2 | * | 11/2005 | Stokes ......................... 607/36 |
| 2003/0204229 | A1 | | 10/2003 | Stokes ........................ 607/122 |

FOREIGN PATENT DOCUMENTS

| EP | 0 791 372 B1 | 1/2004 | ............... A61N 1/05 |
| WO | WO 02/085425 | 10/2002 | |

OTHER PUBLICATIONS

Answers.com, definition of Bulk, pp. 1-8.*
Wang, Lianchun et al., Heparin's anti-inflammaotyr effects require glucosamine 6-O-sulfation and are mediated by blockade of L- and P selectins, pp. 1-24, Journal of Clinical Investigation, vol. 110, Issue 1, Jul. 1, 2002.*
Young, Edward, Thrombosis Research (2008) 122, 743-752.*
Bellec, Gwenaelle, et al., Cancer Letters 100 (1996), pp. 115-123.*
Stokes K, Anderson J, McVenes R, McClay C. "The encapsulation of transvenous polyurethane insulated cardiac pacemaker leads," Cardiovascular Pathology, 4(3):163-172, 1995.
International Search Report for PCT application No. PCT/US2004/006885, Sep. 8, 2004; 3 pgs.
International Preliminary Report on Patentability for PCT application No. PCT/US2004/006885, Sep. 16, 2005; 6 pgs.
Examination Report for European patent application No. 04 718 484.1-1219, Mar. 31, 2006; 4 pgs.
"Bulk," *The Random House College Dictionary*, Urdang et al. eds., Random House, Inc., New York, NY, copyright 1973, p. 178.
Communication Under Rule 71(3) EPC (Intention to Grant a European Patent) for application No. EP 04 718 484.1, Nov. 26, 2010, 4 pgs.
European Office Action for application No. EP 04 718 484.1, Sep. 10, 2007, 5 pgs.

* cited by examiner

*Primary Examiner* — Brian-Yong Kwon
*Assistant Examiner* — Lyndsey Beckhardt
(74) *Attorney, Agent, or Firm* — Carol F. Barry

(57) ABSTRACT

A biostable polymeric substrate of an implantable medical device unit includes a demand-release bioactive composition including one or more bioactive agents covalently bound to surface-modifying end groups of the substrate. Certain cellular activities, in proximity to the polymeric substrate, release substances reacting with the end groups such that the end groups release the one or more bioactive agents, which modify the certain cellular activities.

12 Claims, 5 Drawing Sheets

BULK POLYMER —— OXIDIZABLE —— BIOACTIVE
CHAIN            SME             AGENT

FIG. 1A

BULK POLYMER —— ACID-CATALYZED —— BIOACTIVE
CHAIN            HYDROLYZABLE      AGENT
                 SME

FIG. 1E

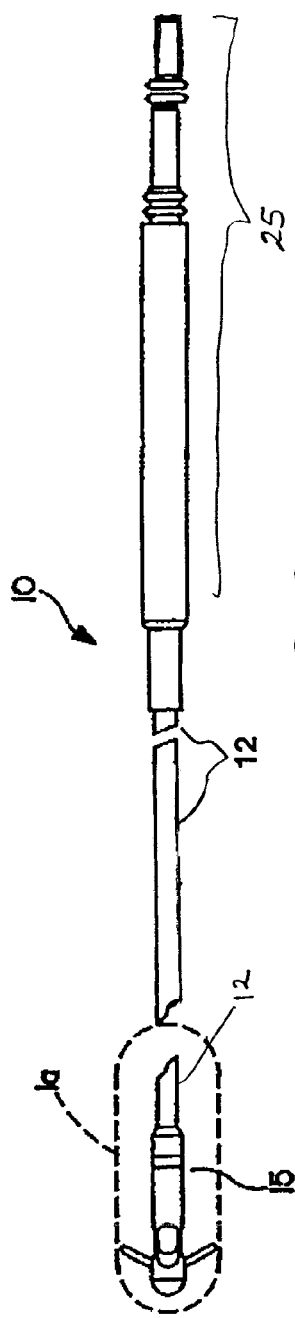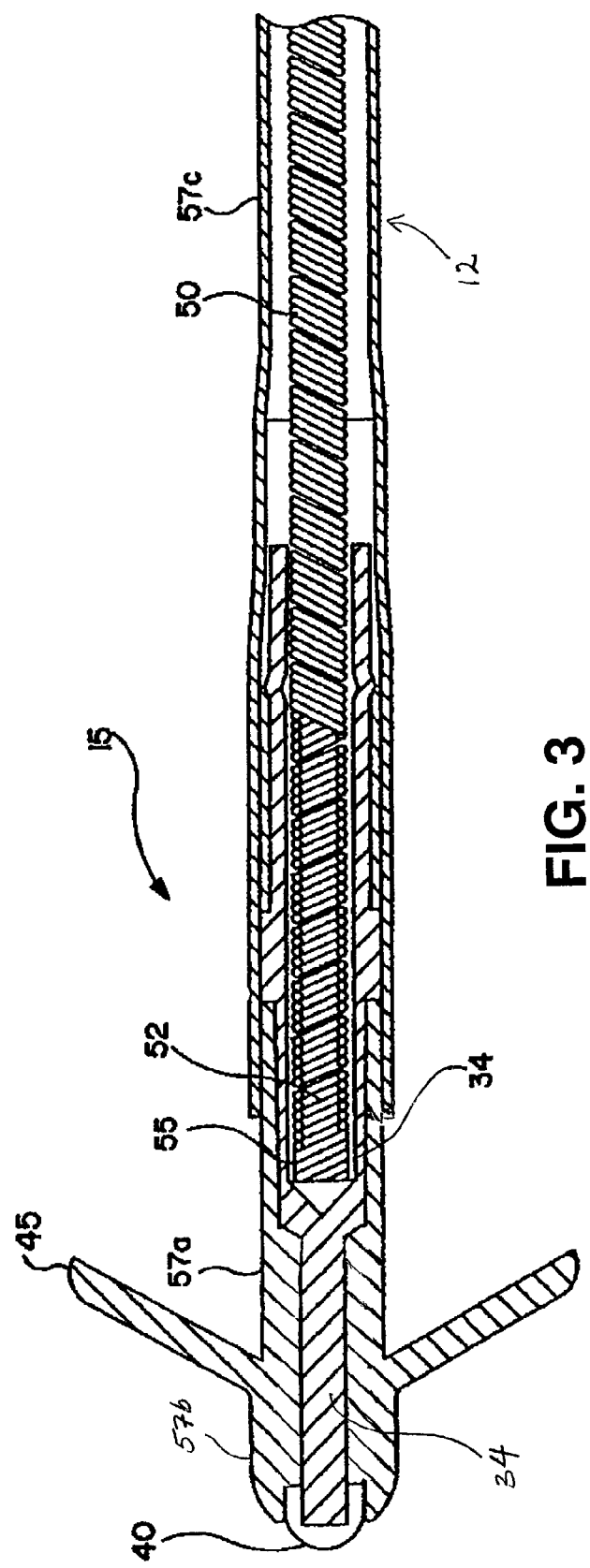

DEMAND-RELEASE BIOACTIVE COMPOSITION FOR IMPLANTABLE MEDICAL DEVICES

FIELD OF THE INVENTION

The present invention relates generally to bioactive polymeric compositions and, more particularly, to a polymeric composition having a covalently bonded, demand-released, bioactive agent for use with body implantable medical devices

BACKGROUND OF THE INVENTION

Biomedical polymer materials are subject to property requirements that may be discussed in terms of bulk property requirements and surface property requirements. The bulk properties must afford a particular medical device with the mechanical characteristics, such as flexibility, toughness, fracture-resistance, tensile strength, etc., needed for a particular application, while the surface properties relate to the biocompatibility of the material with interfacial bodily fluids or tissue. For example, the desired surface properties of a device in contact with blood or tissue may generally include thrombo-resistance, infection-resistance, anti-adhesion or adhesion-promoting properties, lubricious properties, and/or non-inflammatory properties.

Approaches to modifying the surface of a biostable polymer substrate at least partially covering an implantable unit of a medical device include using surface-modifying additives or surface-active endgroups. Polymeric compositions of linear base polymers having covalently bonded surface-active endgroups are disclosed in U.S. Pat. No. 5,589,563 and in International publication WO 02/085425, both of which, in their entireties, are incorporated herein.

Another general approach to achieving improved biocompatibility is to use bioactive coatings. For example antithrombogenic, anti-infection, anti-inflammatory or other bioactive agents may be applied to a polymer surface. Bioactive agents may be ionically bound to a polymeric surface, however, once exposed to blood and bodily fluids, the bioactive molecules bonded in this way may leach away from the surface such that only a transient effect is realized. Bioactive agents may also be covalently bonded to the polymer backbone of the substrate. The bioactive agent may be better immobilized on the polymer substrate by covalent bonding but generally loses its desired effect to some degree because the bioactive molecule has fewer available functional binding sites, reduced mobility, and limited interaction with physiological substrates. An implantable medical device coated with a bioactive material could be improved if the release of the bioactive agent occurred only when needed to combat thrombogenic, inflammatory, or other cellular responses.

One type of implantable unit includes medical electrical leads used for stimulating excitable body tissue for therapeutic purposes such as cardiac pacing, pain control, restoring or reconditioning muscular function, and other purposes. The safety and efficacy of such therapies depends, in part, on the performance of the associated medical lead(s). One factor that can affect lead performance, particularly during the first several weeks after implantation of a lead, is the natural inflammatory response of the body to the lead as a foreign object. The presence of the lead (or other type of implantable medical device) activates macrophages, which attach themselves to the surface of the lead and any electrodes. Some macrophages form multi-nucleated, foreign body giant cells (FBGCs). Macrophages and FBGCs, in turn, secrete various substances, such as hydrogen peroxide as well as various lysosomal enzymes and oxidants, in an effort to break down the foreign object such that the macrophages and FBGCs are able to phagocytose the foreign object. When phagocytosis of the foreign body fails, activated macrophages attract fibroblasts (by chemotaxis) and activate them to lay down a collagenous tissue capsule. This capsule separates the foreign body from the surrounding tissue. Resident macrophages and fibroblasts within the capsule may continue to secrete enzymes for a prolonged period of time, producing a chronic inflammatory response.

Several effects of the acute and chronic inflammatory responses can adversely affect medical lead reliability in regard to both electrode performance and chronic stability of the insulation of lead conductors. At an electrode site, the acute inflammatory response around an electrode surface, can inflict damage to adjacent muscle tissue. Damaged tissue closest to the electrode becomes necrotic. Necrosis provokes further inflammation to exacerbate the tissue damage, significantly increasing acute stimulation thresholds. Chronic stimulation thresholds may be elevated by the development of a collagenous tissue capsule formed around the electrode site. The capsule is not excitable, resulting in an elevated stimulation threshold due to the degraded electrical properties of the electrode-tissue interface.

The insulated portions of a medical lead may also be adversely affected by the foreign body response and chronic inflammation. In the case of cardiac leads, a transvenous lead body, which is implanted in blood, can cause thrombus formation, even if the surface is non-thrombogenic, due to blood stasis or endothelial injury. If the thrombus is in contact with the endothelium, macrophages can invade the clot, phagocytose the blood cells and orchestrate collagenous encapsulation by fibroblasts to stabilize the clot. The foreign body response is initiated with the adhesion and activation of macrophages on the lead body surface, with the subsequent release of oxidants and enzymes intended for breaking down the foreign body. Prolonged exposure to secreted lysosomal oxidants can damage the polymeric insulation of the medical lead in a process known as "environmental stress cracking." Adhesion between the lead and collagenous capsule make lead removal difficult if the lead ever needs to be repositioned or removed.

To address the problems associated with inflammation and the foreign body response at the electrode site, steroid-eluting leads have been introduced. A steroid-eluting porous pacing electrode is generally disclosed in U.S. Pat. No. 4,506,680, issued to Stokes, and related, commonly assigned, U.S. Pat. Nos. 4,577,642 and 4,606,118, all incorporated herein by reference. A water-soluble, anti-inflammatory steroid is retained in a cavity within the lead, preferably in a polymer carrier mounted within a cavity of a tip electrode, and is exposed to body fluids through a porous elution path. A method for coating an electrode with a steroid that is no more than sparingly soluble in water is generally disclosed in U.S. Pat. No. 5,987,746 issued to Williams, incorporated herein by reference in its entirety. The Capsure Z™, Model 5534, steroid-eluting lead available from Medtronic, Inc., includes a tip electrode fabricated of platinized porous platinum deposited with the water soluble steroid dexamethasone sodium phosphate and equipped with a monolithic controlled release device (MCRD) within a cavity of the electrode loaded with the water soluble steroid. Steroid eluting leads present significantly lower peak and chronic stimulation thresholds than non-steroid eluting leads having similarly sized electrodes.

While improving electrode performance, steroid elution near the electrode site does little to prevent encapsulation and environmental stress cracking along the lead body insulation. Elution of a bioactive agent along the entire length or even portions of a medical lead, however, may result in release of an undesired systemic dosage. Furthermore, encapsulation of a lead body in the blood stream may not occur for many years, not until a thrombus forms. (See Stokes K, Anderson J, McVenes R, McClay C. "The encapsulation of transvenous polyurethane insulated cardiac pacemaker leads," *Cardiovascular Pathology*, 4(3):163-172, 1995.) Elution of a bioactive agent in the first weeks after implant would not prevent a late-occurring foreign body response.

It is desirable, therefore, to provide a bioactive composition for use with medical electrical leads, or other types of implantable units of medical devices, which will modify the cellular inflammatory response when it occurs. Since the exact timing of the initiation of a foreign body response is unpredictable, a composition that allows extraction or elution of a bioactive agent at the initiation of the foreign body response is needed. A bioactive composition that improves medical lead performance by reducing or halting the foreign body response and thereby prevents environmental stress cracking, reduces adhesion to ease removability, and/or maintains low stimulation thresholds is desired.

BRIEF DESCRIPTION OF THE DRAWINGS

FIG. 1A is a schematic diagram of a demand-release bioactive composition according to one embodiment of the present invention.

FIG. 1E is a schematic diagram of an alternative embodiment of a demand-release bioactive composition wherein a polymeric backbone is modified with a SME that is oxidatively stable but sensitive to acid hydrolysis.

FIG. 2 is a plan view of an exemplary medical electrical lead system in which polymeric components may be provided with a demand-release bioactive coating or fabricated from a demand-release bioactive bulk material in accordance with the present invention.

FIG. 3 is a cross-sectional view of an electrode assembly portion of the lead system of FIG. 2.

DETAILED DESCRIPTION OF THE INVENTION

Figure 1B:
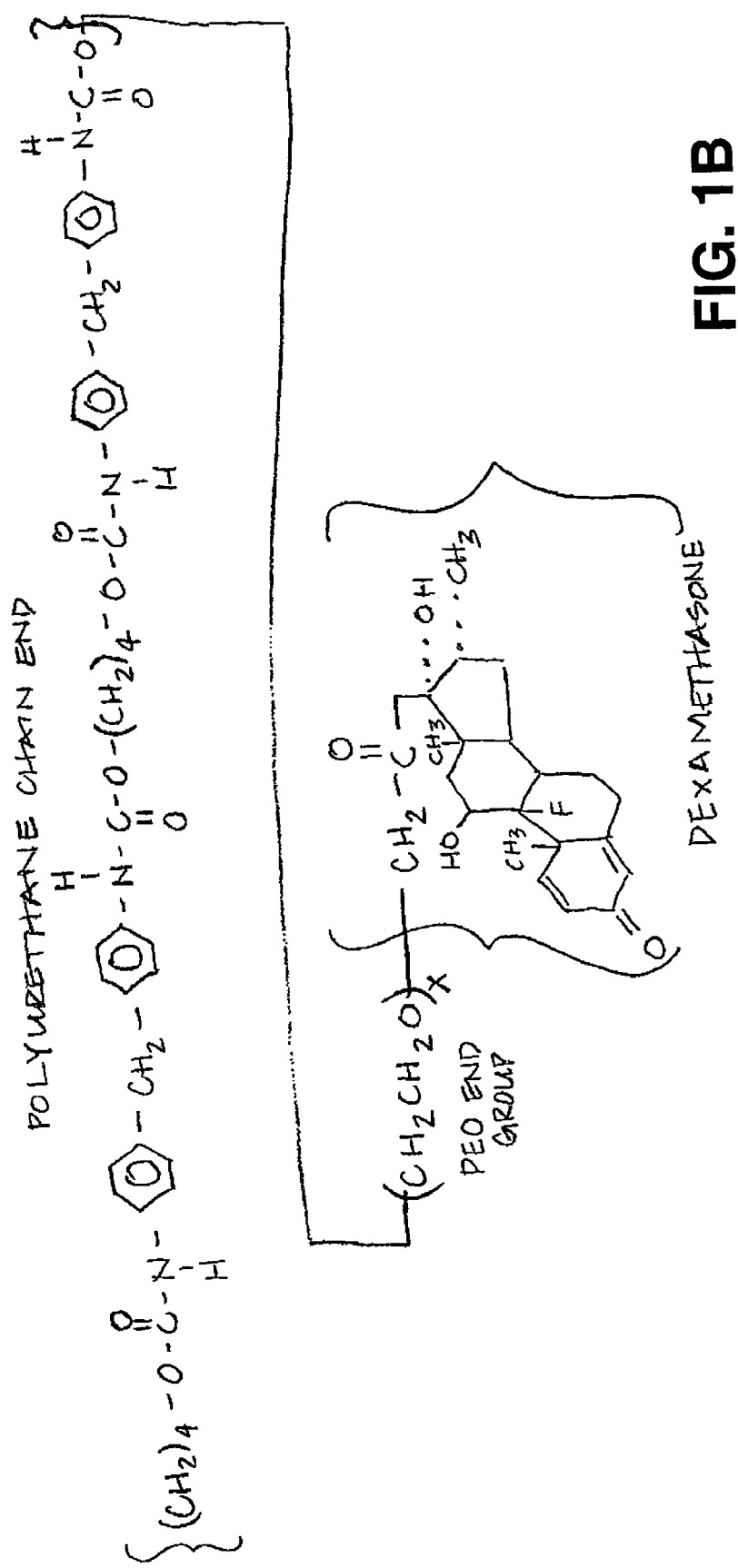
FIG. 1B depicts the chemical structure of a polyurethane chain end modified with a PEO end group to which dexamethasone is covalently bonded.

According to embodiments of the present invention, the release of a bioactive agent occurs upon an initiation of cellular activities associated with events that the bioactive agent is intended to modify. This "on-demand" release of the bioactive agent provides a localized modification of cellular activity, avoiding transient leaching, uncontrolled or unneeded sustained release, or systemic effects of the bioactive agent. Embodiments include medical devices including a demand-release anti-inflammatory coating or bulk material as will be described herein. Furthermore, it is contemplated that other types of bioactive agents could be used in formulating a demand-release bioactive composition that would be beneficial for use with an implantable medical device, such as: collagen to improve removal of the device after chronic implantation; anti-microbial agents to prevent infection; adhesion-promoting agents such as fibronectin to improve fixation and stabilization of the device; anti-adhesion agents such as methyl phosphoryl choline to ease removal after chronic implantation; cytostatic or cytotoxic agents; various enzymes such as urokinase or streptokinase for blood clot lysis; collagenase for breaking down the fibrotic capsule; or anticoagulants such as heparin or albumin to prevent thrombus formation. For a given medical device, one or more bioactive agents could be included in a bioactive composition used to modify one or more cellular responses.

FIG. 1A is a schematic diagram of a demand-release bioactive composition according to one embodiment of the present invention. A polymeric backbone chain is modified with a hydrolytically stable, oxidizable surface modifying endgroup (SME), which forms a spacer between a bioactive agent and the polymeric backbone. A suitable polymeric substrate modified by the SME and bioactive agent is polyether polyurethane, which according to one embodiment of the present invention forms an insulating sheath about a medical electrical lead conductor.

When the modified polymeric material of FIG. 1A is extruded, molded, applied as a coating, or otherwise processed during fabrication of a medical lead or other implantable medical device, the SMEs will migrate to the surface. The bioactive agent is covalently bonded to the SMEs. According to one embodiment, in order to prevent elution of the bioactive agent upon exposure to bodily fluids, the SME is hydrolytically stable. Upon implantation, the SME will remain attached to the substrate polymer, retaining the bioactive agent.

Extraction or elution of the bioactive agent from the surface of the medical device is designed to occur upon the initiation of a cellular activity that the agent is intended to modify. In one embodiment, a bioactive agent is an anti-inflammatory agent, preferably a glucocorticosteroid such as dexamethasone. The anti-inflammatory agent is preferably released to modify cellular inflammatory activity upon initiation of the foreign body response. As such, the hydrolytically stable SME is preferably easily oxidized. The foreign body response is initiated by macrophages attached to the medical device surface. Activated macrophages will release lysosomal enzymes and hydrogen peroxide, hydroxyl radical and super oxide anion, which will oxidize the SMEs, liberating the bioactive agent, in this case an anti-inflammatory agent, that will subsequently modify the inflammatory response. Thus the elution of the bioactive agent will occur only when the foreign body response is initiated. The SME acts as a spacer and as an "on-demand" release agent. An appropriate hydrolytically stable but easily oxidized SME is polyethylene oxide (PEO). Another SME is polymethylene oxide (PMO), which is even more highly oxidizable than PEO. Other oxidizable substances that are hydrolytically stable could be substituted, such as poly(ethylene carbonate).

According to one embodiment, the demand-release bioactive composition is applied to an intra-vascular unit of a medical device. According to an alternate embodiment, the demand-release bioactive composition is within a bulk material included in the medical device. When provided in a bulk material, as the SMEs are consumed at the surface, more SMEs will migrate to the surface. In either case, the SME is preferentially oxidized at the surface, affording a degree of protection to the underlying polymer substrate from the deleterious effects of oxidation. Demand-release of the bioactive agent will act to halt or reduce the release of lysosomal oxidants, preventing or reducing further oxidation.

Figure 1C:
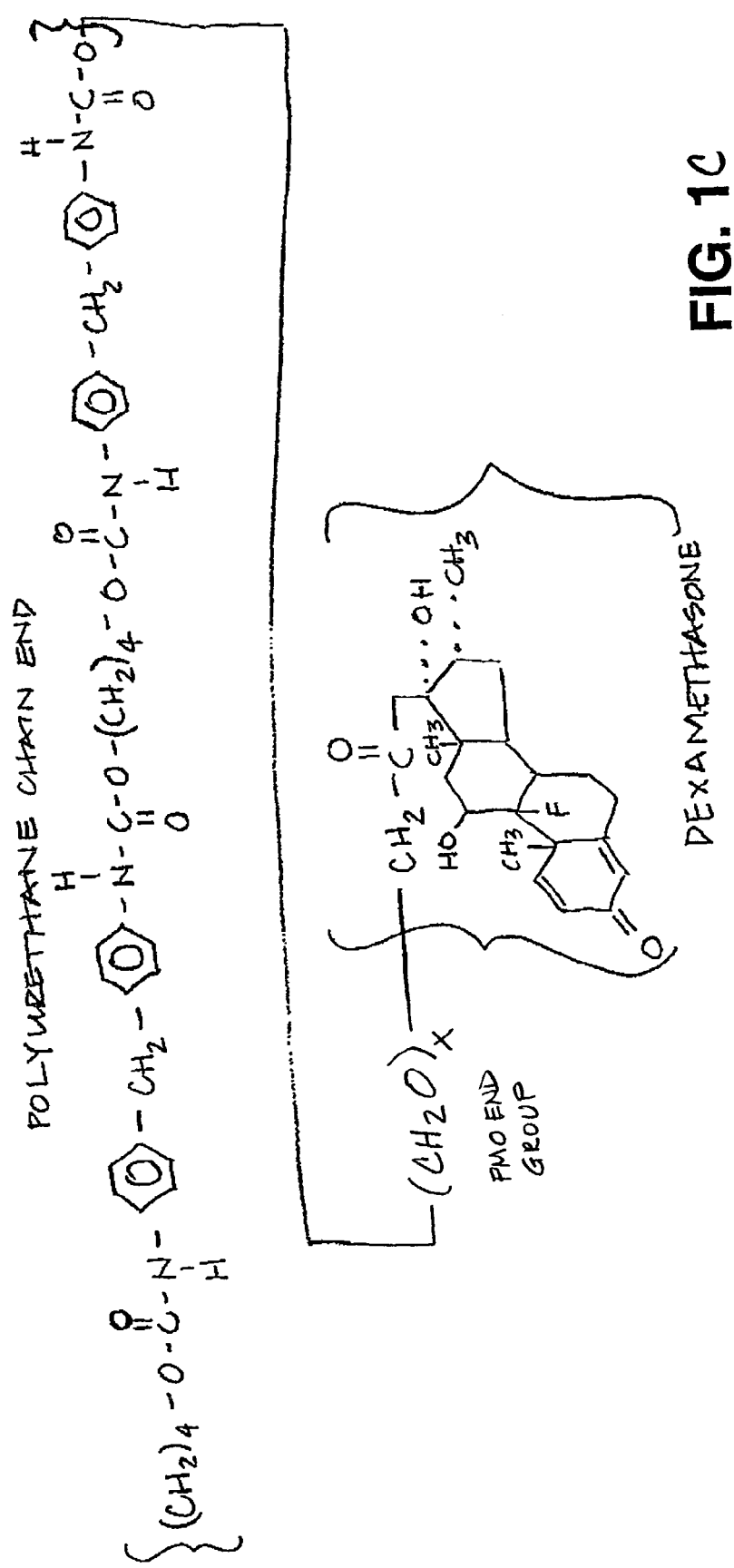
FIG. 1C depicts the chemical structure of a polyurethane chain end modified with a PMO end group to which dexamethasone is covalently bonded.
Figure 1D:
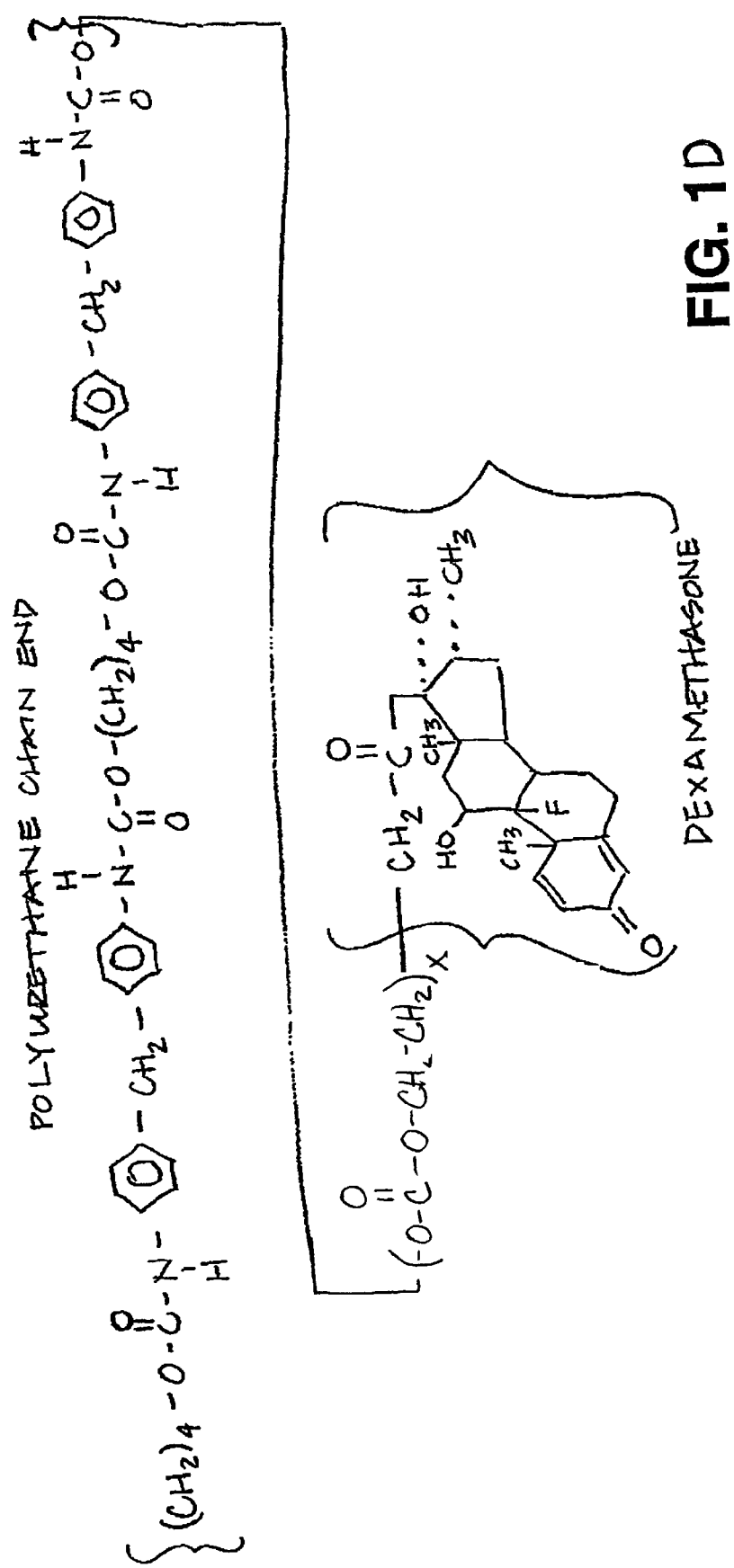
FIG. 1D depicts the chemical structure of a polyurethane chain end modified with a poly(ethylene carbonate) end group to which dexamethasone is covalently bonded.

FIG. 1B depicts the chemical structure of a polyurethane chain end modified with a PEO end group to which dexamethasone is covalently bonded. FIG. 1C depicts the chemical structure of a polyurethane chain end modified with a PMO end group to which dexamethasone is covalently bonded. FIG. 1D depicts the chemical structure of a polyurethane chain end modified with a poly(ethylene carbonate) end group to which dexamethasone is covalently bonded. Upon implantation, the dexamethasone will remain covalently bonded to any of the end groups as shown in FIGS. 1B, 1C, and 1D respectively. The initial step of the inflammatory response is the attachment of macrophages to the device surface. When the macrophages are activated, lysosomal release produces hydrogen peroxide, hydroxy radicals, super oxide anions, and hydrolytic enzymes. According to embodiments of the present invention, the release of these substances will oxidize the PEO or PMO end group liberating the bioactive substance, which, in turn, will halt further lysosomal release terminating the cascade of events in the inflammatory response.

FIG. 1E is a schematic diagram of an alternative embodiment of demand-release bioactive composition wherein a polymeric backbone is modified with an oxidatively stable but acid or enzyme hydrolysis-sensitive SME forming a spacer between the substrate polymer and a bioactive agent. The pH under a macrophage is highly acidic compared to the normal pH of the surrounding blood environment. Therefore, a SME that is subject to acid catalyzed hydrolysis would release a bioactive agent to halt further lysosomal release upon macrophage activation. Such SMEs may include, but are not limited to, ester or amide based groups, e.g. acetal or acrylic esters.

FIG. 2 is a plan view of an exemplary medical electrical lead 10. As illustrated in FIG. 2, lead 10 includes an elongated lead body 12, a connector 25 and an electrode assembly 15. FIG. 3 is a section view of a portion of lead 10. In FIG. 3, a distal portion of lead body 12 and electrode assembly 15 are shown in greater detail. FIG. 3 illustrates lead body 12 including conductor 50 and an outer insulation 57c and electrode assembly 15 including an electrode 40, a conductive element 34, insulation elements 57a and 57b, and a tine 45 to stabilize electrode 40 when lead 10 is implanted. As further illustrated, conductive element 34 couples a distal end 55 of lead conductor 50, which extends the length of lead body 12, to electrode 40. Lead conductor 50 is also similarly attached at a proximal end (not shown) to connector 25. According to one embodiment of the present invention outer insulation 57c is formed of a biostable polymeric substrate and all or a portion of outer insulation 57c includes a demand-release bioactive agent covalently bound to SME's. According to other embodiments, insulation elements 57a and/or 57b and/or tines 45 are formed of biostable polymeric substrates and all or a portion of insulation elements 57a and/or 57b and/or tines 45 includes a demand-release bioactive agent covalently bound to SME's. According to one embodiment of the present invention, outer insulation 57c and insulation elements 57a and 57b are formed from polyurethane.

Bioactive agents included in outer insulation 57c, insulation elements 57a, 57b, and tines 45 will only be released where SME's undergo oxidation or acid catalyzed hydrolysis following macrophage activation. The release of the bioactive agent will be localized to an area where macrophages are activated. Thus, a controlled, "on-demand" release of the bioactive agent having localized elution is realized.

In one embodiment, insulation element 57b is fabricated from a demand-release bioactive material or provided with a demand-release bioactive coating. In addition, electrode 40 is provided with a coating of a steroid, such as dexamethasone sodium phosphate. An elutable steroid coating may be applied to electrode 40 according to methods known in the art. The steroid coating is provided to diminish the effects of the acute inflammatory response. The demand release bioactive material is provided to diminish the effects of the foreign body response and chronic inflammation. In this way, elevation of acute and chronic stimulation thresholds is avoided without the use of additional special components, such as a monolithic controlled release device, for controlling the elution of an anti-inflammatory agent. In alternate embodiments, non-water soluble steroids such as dexamethasone acetate and beclomethasone diproprionate are applied as a steroid coating to electrode 40.

While specific embodiments of the present invention have been described herein, it is recognized that numerous variations may be made using the principles of the present invention. The descriptions provided herein should, therefore, be considered exemplary, not limiting, with regard to the following claims.

We claim:

1. A medical device comprising:
    an implantable unit comprising a bulk polymeric material including surface-modifying end groups provided throughout the bulk of the polymeric material; and
    a demand-release bioactive composition provided within and throughout the bulk of the polymeric material included in the implantable unit, wherein the demand-release bioactive composition includes one or more bioactive agents covalently bound to the surface-modifying end groups, wherein the one or more bioactive agents are released when the surface-modifying end groups undergo one of oxidation, acid-catalyzed hydrolysis, or enzyme-catalyzed hydrolysis;
    wherein certain cellular activities, in proximity to the polymeric substrate, release substances reacting with the surface-modifying end groups such that the surface-modifying end groups release the one or more bioactive agents, which modify the certain cellular activities;
    wherein the cellular activities are initiated by macrophage activation; and
    wherein the one or more bioactive agents are only released when the surface-modifying end groups undergo oxidation, acid-catalyzed hydrolysis, or enzyme-catalyzed hydrolysis following macrophage activation,
    wherein the surface-modifying end groups are hydrolytically stable and oxidizable,
    wherein the surface modifying end group comprises polymethylene oxide, and
    wherein the one or more bioactive agents are bound to the polymethylene oxide.

2. The medical device of claim 1, wherein the implantable unit includes an intra-vascular portion.

3. The medical device of claim 1
    wherein the polymeric material is a biostable polymeric material; and
    wherein the one or more bioactive agents comprises one or more bioactive anti-inflammatory agents.

4. The medical device of claim 3, wherein the implantable unit includes an intra-vascular portion.

5. The medical device of claim 1, wherein the one or more bioactive agents comprises an enzyme.

6. The medical device of claim 1, wherein the one or more bioactive agents comprises collagenase.

7. The medical device of claim 1, wherein the one or more bioactive agents comprises an anti-inflammatory agent.

8. The medical device of claim 3, wherein elevation of acute and chronic stimulation thresholds is avoided without the use of a monolithic controlled release device.

9. The medical device of claim 1, wherein elevation of acute and chronic stimulation thresholds is avoided without the use of a monolithic controlled release device.

10. The medical device of claim 1, wherein upon consumption of surface-modifying end groups at the surface of the polymeric material, additional surface-modifying end groups migrate from the bulk of the polymeric material to the surface of the polymeric material.

11. A medical device comprising:
   an implantable unit;
   a biostable polymeric substrate at least partially covering the unit and including surface-modifying end groups; and
   a demand-release bioactive composition comprising one or more bioactive agents covalently bound to the surface-modifying end groups;
   wherein the surface-modifying end groups are hydrolytically stable and oxidizable, such that cellular activities that occur in proximity to the polymeric substrate release substances that react with the surface-modifying end groups causing the surface-modifying end groups to release the one or more bioactive agents, which modify the certain cellular activities upon their release;
   wherein the cellular activities are initiated by macrophage activation; and
   wherein the surface modifying end groups are configured to release the one or more bioactive agents when the surface-modifying end groups undergo oxidation following macrophage activation,
   wherein the surface modifying end groups comprise polymethylene oxide, and
   wherein the one or more bioactive agents are bound to the polymethylene oxide.

12. The medical device of claim 11, wherein the one or more bioactive agents comprises an anti-inflammatory agent.

* * * * *